US010542917B2

(12) United States Patent
Schimmoeller et al.

(10) Patent No.: US 10,542,917 B2
(45) Date of Patent: Jan. 28, 2020

(54) PRINTED CIRCUIT BOARD WITH EMBEDDED SENSOR

(71) Applicant: Battelle Memorial Institute, Columbus, OH (US)

(72) Inventors: Andrew M. Schimmoeller, Plain City, OH (US); Jeffrey A. Friend, Grove City, OH (US)

(73) Assignee: Battelle Memorial Institute, Columbus, OH (US)

( * ) Notice: Subject to any disclaimer, the term of this patent is extended or adjusted under 35 U.S.C. 154(b) by 114 days.

(21) Appl. No.: 15/116,737

(22) PCT Filed: Feb. 10, 2015

(86) PCT No.: PCT/US2015/015180
§ 371 (c)(1),
(2) Date: Aug. 4, 2016

(87) PCT Pub. No.: WO2015/120439
PCT Pub. Date: Aug. 13, 2015

(65) Prior Publication Data
US 2016/0345875 A1 Dec. 1, 2016

Related U.S. Application Data

(60) Provisional application No. 61/937,663, filed on Feb. 10, 2014.

(51) Int. Cl.
*A61B 5/05* (2006.01)
*A61B 5/145* (2006.01)
(Continued)

(52) U.S. Cl.
CPC ........ *A61B 5/14503* (2013.01); *A61B 5/0031* (2013.01); *A61B 5/01* (2013.01);
(Continued)

(58) Field of Classification Search
CPC ........ A61B 2562/164; A61B 2562/166; A61B 5/14503; A61B 5/14542
See application file for complete search history.

(56) References Cited

U.S. PATENT DOCUMENTS 6,494,829 B1 * 12/2002 New, Jr. ............... A61B 5/0002
128/903
6,889,165 B2 5/2005 Lind et al.
(Continued)

FOREIGN PATENT DOCUMENTS

DE 102010048768 A1 4/2012
EP 1477048 B1 6/2011
(Continued)

OTHER PUBLICATIONS

Joyce Laird, Medical Electronics on the Bleeding Edge, http://medicaldesign.com/print/electronics/medical-electronics-bleeding-edge, Sep. 8, 2016, pp. 1-6.
(Continued)

*Primary Examiner* — Michael J D Abreu
(74) *Attorney, Agent, or Firm* — Fay Sharpe LLP

(57) ABSTRACT

A sensing device includes a printed circuit board (PCB) having a conductive trace. A micro-controller is attached to the conductive trace and data transmission means is connected to the micro-controller. A sensor is embedded within the PCB and is connected to the micro-controller via the conductive trace. The sensor is configured to sense at least one physiological parameter in a patient.

23 Claims, 7 Drawing Sheets

(51) Int. Cl.
| | |
|---|---|
| *A61B 5/00* | (2006.01) |
| *H05K 1/18* | (2006.01) |
| *A61B 5/01* | (2006.01) |
| *A61B 5/021* | (2006.01) |
| *A61B 5/03* | (2006.01) |
| *A61B 5/04* | (2006.01) |
| *A61B 5/0402* | (2006.01) |
| *A61B 5/08* | (2006.01) |
| *H05K 1/02* | (2006.01) |

(52) U.S. Cl.
CPC .............. *A61B 5/021* (2013.01); *A61B 5/036* (2013.01); *A61B 5/04001* (2013.01); *A61B 5/0402* (2013.01); *A61B 5/08* (2013.01); *A61B 5/14532* (2013.01); *A61B 5/14542* (2013.01); *A61B 5/4266* (2013.01); *A61B 5/6848* (2013.01); *A61B 5/7282* (2013.01); *H05K 1/0298* (2013.01); *H05K 1/183* (2013.01); *A61B 2560/0219* (2013.01); *A61B 2562/164* (2013.01); *A61B 2562/166* (2013.01); *H05K 2201/10037* (2013.01); *H05K 2201/10151* (2013.01); *H05K 2201/10242* (2013.01)

(56) References Cited

U.S. PATENT DOCUMENTS

| | | | |
|---|---|---|---|
| 8,214,007 B2* | 7/2012 | Baker | A61B 5/0006 600/372 |
| 8,368,201 B2 | 2/2013 | Tuominen | |
| 8,599,572 B2 | 12/2013 | Neudecker et al. | |
| 2011/0176037 A1* | 7/2011 | Benkley, III | G06K 9/0002 348/294 |
| 2011/0213225 A1* | 9/2011 | Bernstein | G06Q 50/22 600/309 |
| 2013/0109997 A1 | 5/2013 | Linke et al. | |
| 2013/0274567 A1 | 10/2013 | Grosser et al. | |
| 2013/0343022 A1 | 12/2013 | Hu et al. | |
| 2014/0011951 A1 | 1/2014 | Martens et al. | |

FOREIGN PATENT DOCUMENTS

| | | |
|---|---|---|
| WO | 9956613 A1 | 11/1999 |
| WO | 02076289 A2 | 10/2002 |

OTHER PUBLICATIONS

PCT International Search Report and Written Opinion, Application No. PCT/US2015/015180, dated Apr. 24, 2015.

* cited by examiner

US 10,542,917 B2

PRINTED CIRCUIT BOARD WITH EMBEDDED SENSOR

BACKGROUND

This invention relates in general to printed circuit boards (PCBs). In particular, this invention relates to an improved PCB that includes an embedded sensor and is configured as a sensing device to be carried, worn, affixed to, inserted into, or implanted in a user.

Companies that use and/or manufacture PCBs are making the decision to add the technical capability of embedded components technology to their design portfolios. This decision is driven by a number of advantages gained by using embedded technology, including the need for smaller size, higher component density, improved electrical performance, and overall cost reduction. The embedded component technology offers companies an alternative to an Application-Specific Integrated Circuit; i.e., an integrated circuit that is customized for a particular use, rather than intended for general-purpose use. Such embedded component technology provides companies benefits similar to those provided by Application-Specific Integrated Circuits, but with a shorter development timeframe and a lower cost than conventional PCBs.

For example, multi-layered PCBs may include fully or partially embedded active and/or passive components. Such active components may include any component that is capable of providing a powered functionality, such as a controller or other transistor-based circuits. Passive components may include components that cannot provide any power gain to the circuit, and need the help of active devices to operate, such as resistors, inductors, and capacitors. Other components may include an energy source, such as a battery or a capacitor.

Conventional PCBs with embedded active and/or passive components are described in the publication "IPC-7092; Design and Assembly Process Implementation for Embedded Components," Working Draft dated 1 May 2013, published by IPC (also known as Association Connecting Electronics Industries).

It would however, be desirable to provide an improved structure for a PCB that that may be configured as a sensing device and that includes an embedded sensor to measure one or more designated physiological parameters, is compact, readily configurable to be carried, worn, affixed to, inserted into, or implanted in the user, yet remains relatively simple and inexpensive.

SUMMARY

This invention relates in general to printed circuit boards (PCBs) and sensing devices made therefrom. In particular, this invention relates to an improved sensing device formed from PCB that includes an embedded sensor and is configured to be carried, worn, affixed to, inserted into, or implanted in a user.

In one embodiment, a sensing device includes a printed circuit board (PCB) having a conductive trace. A micro-controller is attached to the conductive trace and data transmission means is connected to the micro-controller. A sensor is embedded within the PCB and is connected to the micro-controller via the conductive trace. The sensor is configured to sense at least one physiological parameter in a patient.

Various advantages of the invention will become apparent to those skilled in the art from the following detailed description, when read in view of the accompanying drawings.

DETAILED DESCRIPTION

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Figure 1:
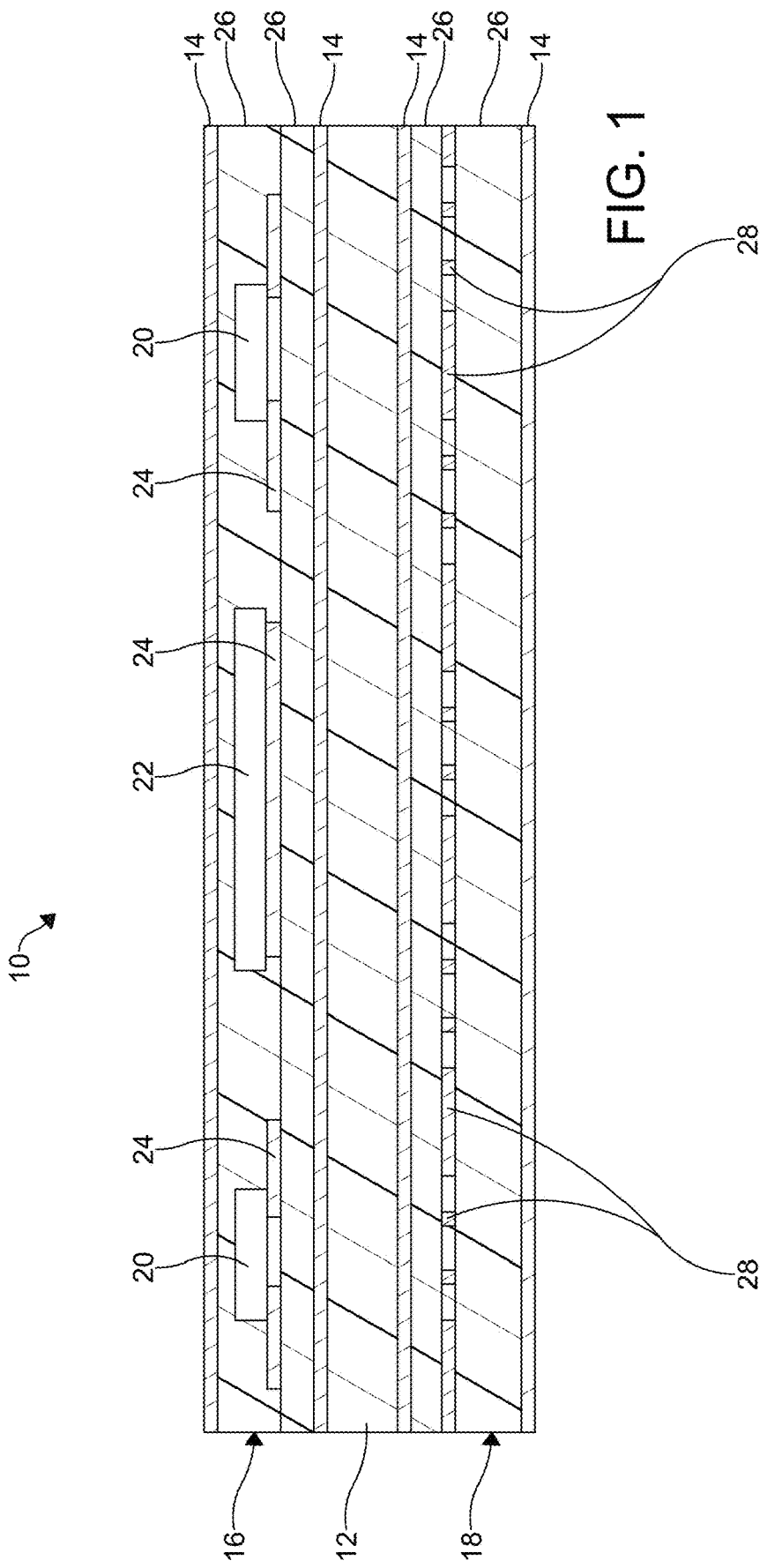
FIG. 1 is an elevational view in cross section of a conventional PCB with components embedded therein.

Referring now to the drawings, there is illustrated in FIG. 1 a basic structure of a conventional PCB 10 with components embedded therein. In the embodiment illustrated in FIG. 1, the PCB 10 includes a four-layer mounting base onto which both active and passive components, described below, have been attached.

The PCB 10 includes a base-core 12 formed from a dielectric material with copper, such as copper foil 14 bonded to both sides. The base-core 12 may be any desired dielectric material, such as a cured (hardened) fiberglass—weave material with epoxy resin.

A first dielectric layer 16 is attached to a first side (upper side when viewing FIG. 1) of the base-core 12, and a second dielectric layer 18 is attached to a second side (lower side when viewing FIG. 1) of the base-core 12. Layers of copper, such as the copper foil 14 are bonded to the outside surfaces of the first and second dielectric layers 16 and 18, respectively. Thus, with the addition of copper foil 14 to the first and second dielectric layers 16 and 18, the PCB 10 is configured as with six conductive, i.e., copper, layers.

The first dielectric layer 16 includes passive components 20 and active components 22 (only one of which is shown in FIG. 1) connected to a first conductive trace 24 and embedded in one or more layers of prepreg 26. The second dielectric layer 18 includes one or more layers of prepreg 26, and may include a second conductive trace 28 therein.

Other configurations of conventional PCBs with components embedded therein are known and described in the publication "IPC-7092; Design and Assembly Process Implementation for Embedded Components," published by IPC (also known as Association Connecting Electronics Industries).

As used herein, prepreg is a reinforced or non-reinforced, uncured glass fiber material. The prepreg acts as an insulating layer and provides a bonding agent for joining layers of the PCB 10 together.

As used herein, an embedded component is a component that is positioned within one or more of the layers of the PCB 10, rather than being positioned on an outside surface of the PCB 10. Embedded is further defined as being integrally formed within one or more of the layers of the PCB 10, or being inserted into a cavity formed in one or more of the layers of the PCB 10. A partially embedded component is a component wherein a portion of the component is integrally formed within one or more of the layers of the PCB 10, or a portion of the component is inserted into a cavity formed in one or more of the layers of the PCB 10, and wherein a portion of the component extends outwardly of an outer surface of the PCB 10, or wherein a portion of the component may not extend outwardly of the outer surface of the PCB 10, but is exposed through the outer surface of the PCB 10.

It will be understood that both an embedded component and a partially embedded component include electrical connectors, such as terminals, that are configured to be connected to one or more electrically conductive layers of the PCB 10.

As used herein, and as defined in IPC-7092, an active component is an electronic component that can change a signal or respond to the signal in a way that is dependent upon the nature of the signal and/or other controlling factors. Examples of active components include diodes, transistors, amplifiers, thyristors, gates, Application-Specific Integrated Circuits, semiconductor chips, micro-controller, and other integrated circuits that are used for the rectification, amplification, and switching of analog or digital circuits.

As used herein, and as defined in IPC-7092, a passive component is a discrete electronic device that behaves in a fixed way in response to a signal of a given characteristic. Examples of passive components include resistors, capacitors, inductors, and transformers.

Figure 2:
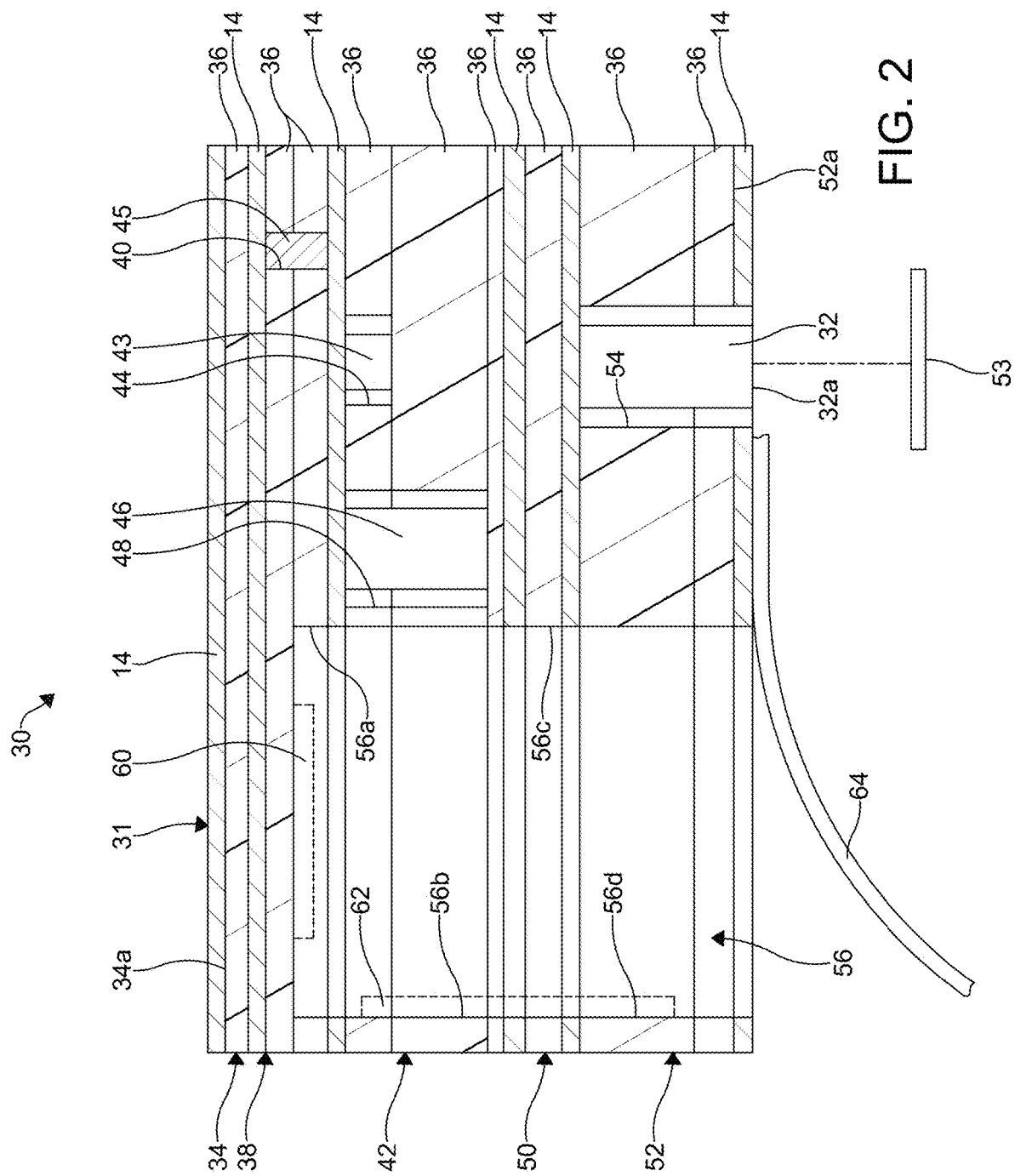
FIG. 2 is an elevational view in cross section of a first embodiment of the sensing device in accordance with this invention.
Figure 5:
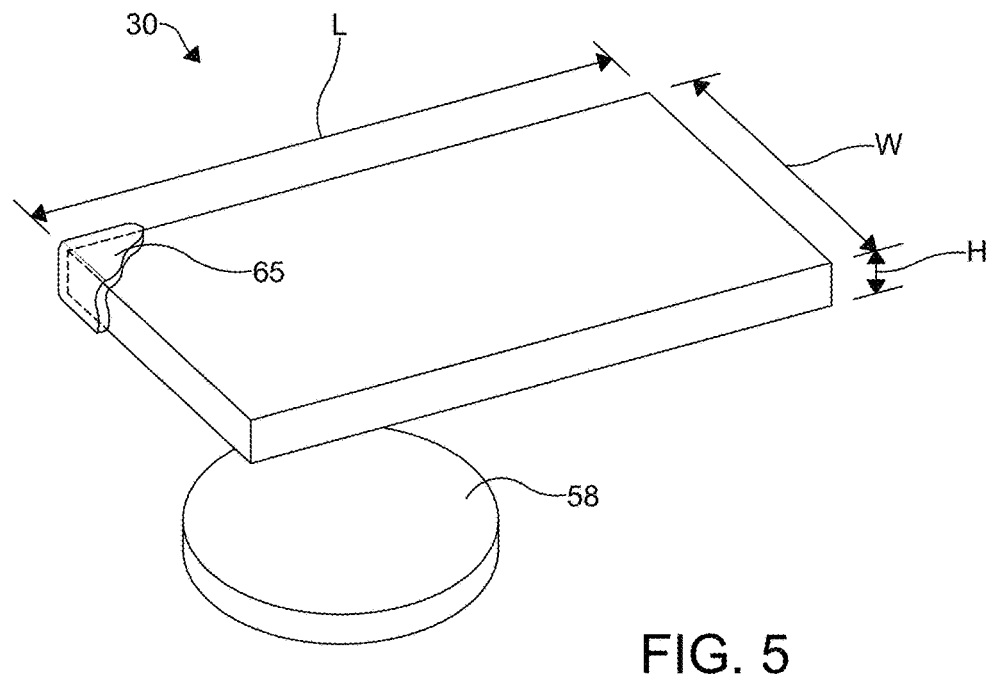
FIG. 5 is a perspective view of the sensing device illustrated in FIG. 2 with a battery shown uninstalled.

Referring to FIGS. 2 and 5, a first embodiment of an improved PCB is shown at 30. The improved PCB 30 is configured for use as a sensing device and includes many of the features of the conventional PCB 10 described above, but advantageously includes one or more sensors 32 embedded or partially embedded therein. The sensor 32 may be any desired sensor for detecting and/or measuring a physiological parameter, such as temperature, heart rate, blood pressure, oxygen saturation of blood (e.g., pulse-ox), respiration, electrical activity of the heart (such as would be determined by a conventional electrocardiogram), body movement (e.g., angle, acceleration, state of activity), blood attributes (such as attributes determined in conventional blood panel screening), internal body pressures or organ activity, glucose levels, perspiration, neural activity, neural stimulation, infection, and other desired physiological parameters.

The embodiments of the improved PCB 30 described and illustrated herein may be configured for medical purposes, such as for detecting and/or measuring any of the physiological parameters described above in a human patient. Additionally, the embodiments of the improved PCB 30 described and illustrated herein may include a sensor 32 configured to electrically stimulate a patients nerves.

In FIG. 2, the first embodiment of the improved PCB 30 is not illustrated to scale, and the component layers are shown having an exaggerated thickness for clarity. As best shown in FIG. 2, the first embodiment of the improved PCB 30 includes a substrate 31 having a plurality of dielectric layers. The illustrated substrate 31 includes a first dielectric layer 34 comprising at least one layer of prepreg 36. A second dielectric layer 38 includes two layers of prepreg 36 and has a via 40 formed therethrough. A third dielectric layer 42 includes three layers of prepreg 36 and has one or more components embedded therein. In the illustrated embodiment, a first component 43 is mounted within a first cavity 44 and a second component 46 is mounted within a second cavity 48. As described above, the components 43 and 46 may be inserted in the cavities 44 and 48, or the components 43 and 46 may be integrally formed with the layers of prepreg 36.

In the illustrated embodiment, the first component 43 is any of the passive components described above, and the second component 46 is an active component, such as a micro-controller, or any of the other active components described above. A fourth dielectric layer 50 includes at least one layer of prepreg 36. A fifth dielectric layer 52 includes two layers of prepreg 36 and has one or more sensors 32 embedded or partially embedded therein.

Layers of conductive material, such as the copper foil 14, are bonded to first and second outside surfaces 34a and 52a, of the first and fifth dielectric layers 34 and 52, respectively. Layers of copper foil 14 are also bonded between the first and second dielectric layers, 34 and 38, between the second and third dielectric layers, 38 and 42, between the third and fourth dielectric layers, 42 and 50, and between the fourth and fifth dielectric layers, 50 and 52. In the illustrated embodiment, the embedded layers of the copper foil 14 define conductive traces within the PCB 30, and to which electronic components may be attached. Although the layer 14 is described as being formed from copper foil, it will be understood that the layer 14 may be formed from any other suitable form of copper, and any other desired conductive material.

The via 40 is filled with a conductive material 45, such as copper, that extends between two layers of copper foil 14. The layers of copper foil 14 are bonded respectively to the first and second outside surfaces 34a and 52a of the first and fifth dielectric layers 34 and 52, may function as shielding, such as EMI shielding for the PCB 30. It will be understood that such shielding may be embedded within the PCB 30 as one or more layers of the PCB 30.

Figure 3A:
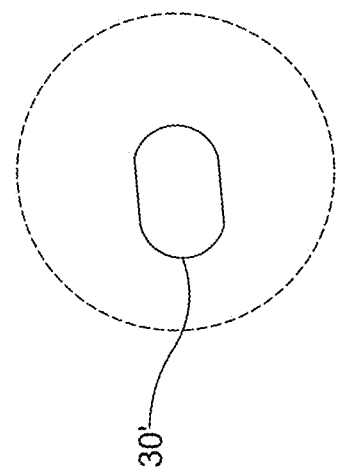
FIG. 3A is an enlarged view of the device in the circle 3A in FIG. 3.
Figure 3:
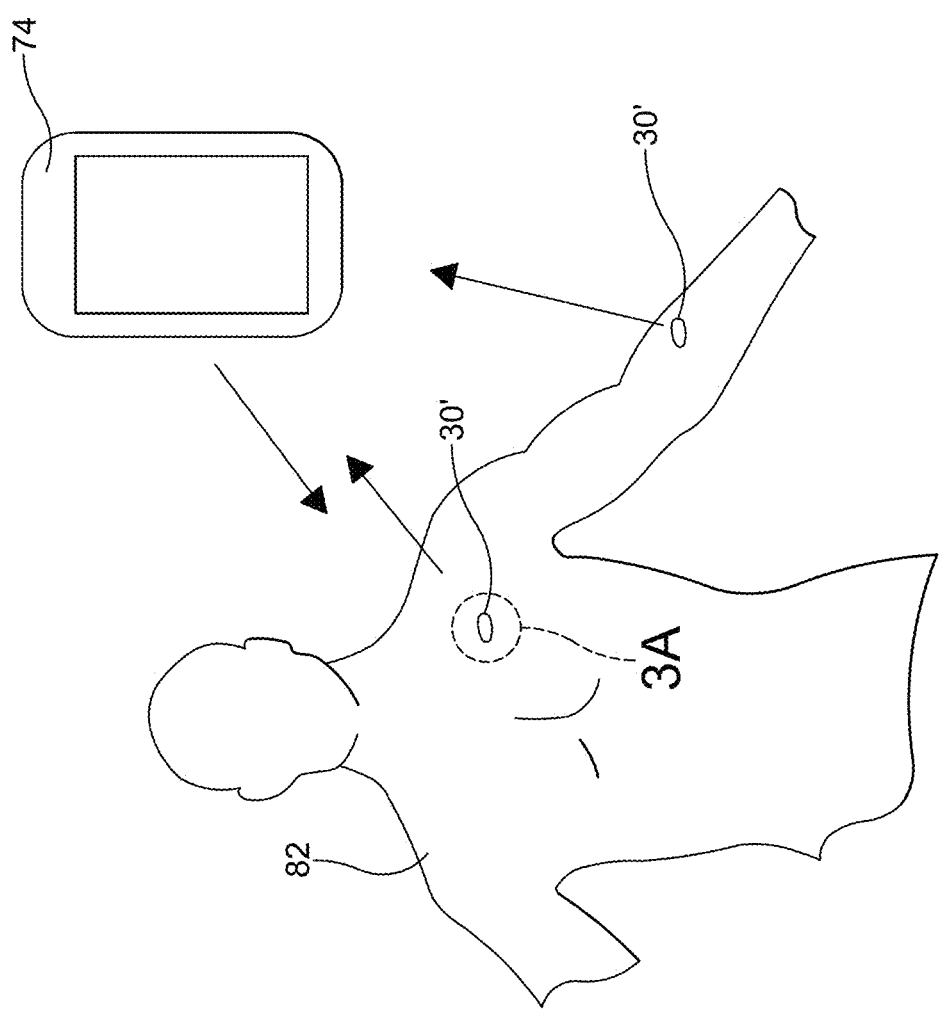
FIG. 3 is an elevational view showing one application for a second embodiment of a sensing device in accordance with this invention.
Figure 4:
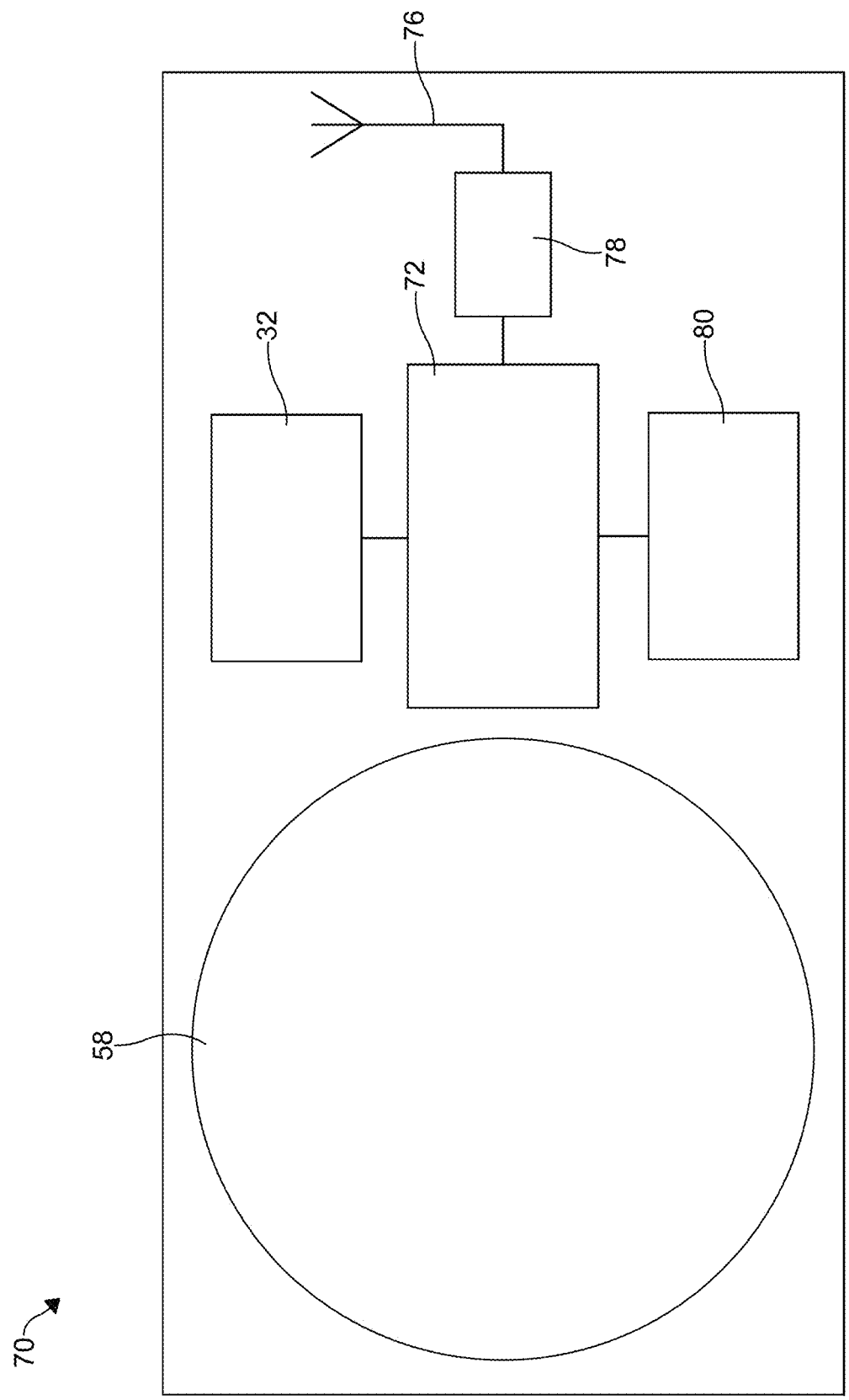
FIG. 4 is a block design of the device illustrated in FIG. 3.

Like the components 43 and 46, the sensor 32 may be inserted in a third cavity 54, or the sensor 32 may be integrally formed with the layers of prepreg 36. As shown, the sensor 32 is partially embedded in the fifth dielectric layer 52 such that an end surface 32a of the sensor 32 is exposed through the second outside surface 52a. As will be explained in detail below, the end surface 32a is exposed through the second outside surface 52a to be in intimate contact with, or in close proximity to, the skin of a patient 82, such as shown in FIG. 3.

The sensor 32 may be any desired sensor for detecting and/or measuring a physiological parameter, such as those described above. Advantageously, the PCB 30 is configured such that it can include one or more of any type of sensor.

One or more of such sensors 32 may be embedded or partially embedded in the PCB 30.

If desired, a membrane 53 may be bonded to the second outside surface 52a to cover the third cavity 54 and the sensor 32 therein. The membrane 53 may be any desired material, such as a conductive polymer, metal, hydrogel, or an optical guide. As used herein, an optical guide may be any translucent or transparent material that allows the transmission of light, such as an optical signal to and from an optical sensor. Alternatively, the membrane 53 may be formed from any organic or inorganic material that allows the sensor 32 to sense the physiological parameter for which it is designed to sense.

As also shown in FIG. 2, cavities 56a, 56b, 56c, and 56d are formed through a portion of the second dielectric layer 38 and through the third, fourth, and fifth dielectric layers 42, 50, and 52, respectively, to define a battery well 56 into which a battery, such as the battery 58 shown in FIG. 5 may be inserted. The battery 58 may be any desired battery, such as a coin-cell battery or a rechargeable cell battery. Alternatively, other sources of electrical energy may be provided in lieu of the battery 58. Examples of such other sources of electrical energy include capacitors, inductive couplings, and tuned antennas.

Electrical contact surfaces may be provided at any location in the battery well 56, such as at 60 on a bottom of the battery well 56, and/or at 62 on a side wall of the battery well 56. Additionally, electrical contact surfaces may be integrally formed in the various layers of the PCB 30, such as the portions of the copper foil 14 that extend to the battery well 56.

The battery 58 may be retained in the battery well 56 by any desired means, such as with an interference fit, a spring clip (not shown), adhesive, or with tape, such as conductive tape 64.

If desired, all or any portion of the outer surfaces of the PCB 30 may be coated with a layer of protective material 65, a portion of which is shown in FIG. 5. Materials suitable for use as the layer of protective material 65 include plastic, glass, and biocompatible or electrically insulating conformal coatings. Additionally, the PCB 30 and components thereof may be coated with a layer of any material that protects against moisture, dust, chemicals, and temperature extremes that, if not protected, could result in damage or failure of the PCB 30 and/or any component of the PCB 30. It will be understood that the assembled PCB 30, with or without the layer of protective material 65 defines a sensing device suitable for use with human patients.

Figure 6:
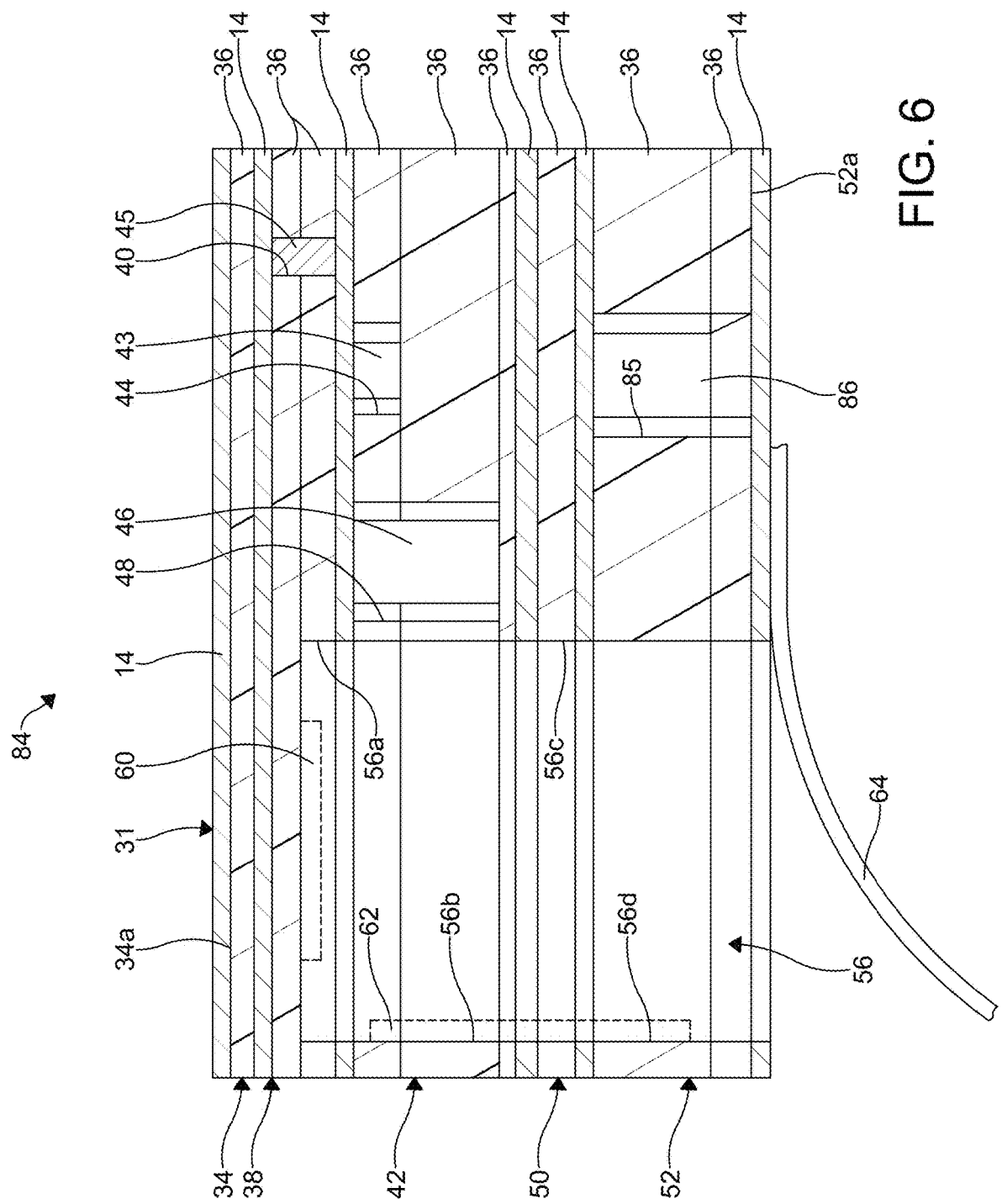
FIG. 6 is an elevational view in cross section of a third embodiment the sensing device illustrated in FIG. 2.

As best shown in FIG. 6, the PCB 30 may have the shape of a rectangular prism. Alternatively, the PCB 30 may have any other desired shape, such as the PCB 30' in FIG. 3 wherein the ends are rounded, thereby eliminating sharp corners. Additionally, the PCB 30 may have any other shape, such as required to conform to the contour of the human body.

Advantageously, the improved PCB 30 may be made in a very small size, so that it can be easily carried, worn, affixed to, inserted into, or implanted in a user or patient 82, as described below. For example, the PCB 30 may have a length L within the range of from about 5 mm to about 25 mm, a width W within the range of from about 5 mm to about 25 mm, and a thickness T within the range of from about 1 mm to about 10 mm. It will be understood however, that the length L, width W, and thickness T, may be smaller or larger depending on the application and the size and number of components and sensors embedded in the PCB 30.

The embodiment of the PCB 30 described above is a rigid PCB. It will be understood however, that the PCB 30 maybe formed as a flexible PCB or as a semi-flexible PCB. Additionally, the PCB 30, and any of the embodiments of the improved PCB described herein, may be formed in a 3D printer from a combination of any dielectric and conductive materials suitable for use in such a 3D printer.

A second embodiment of the improved PCB is shown schematically at 70 in FIG. 3. In addition to conventional power conditioning circuitry required to make the improved PCB 70 functional, the sensor 32, and the battery 58, the improved PCB 70 may include a micro-controller 72 with Bluetooth capability, such as Bluetooth Low Energy (BLE), to communicate with a portable electronic device; i.e., a receiver, such as a smart phone (74 in FIG. 3), a tablet (not shown), or other computer (not shown). The micro-controller 72 may also be configured to control operation of the sensor 32 and to process data received from the sensor 32. Alternatively, other data transmission means, or means to communicate with the portable electronic device, such as the smart phone 74, may be provided. Such other means may include near field communications and other wireless communications devices. The PCB 70 may include an antenna 76 connected to the micro-controller 72, and if desired, a BALUN 78 to stabilize the transmission of data. The PCB 70 may also include a crystal or oscillator 80 to support the operation of the micro-controller 72.

A third embodiment of the improved PCB is shown at 84 in FIG. 6. The PCB 84 is substantially similar to the PCB 30, but includes a sensor 86 inserted in a cavity 85. Like the sensor 32 in the PCB 30, the sensor 86 may be integrally formed with the layers of prepreg 36. As shown, the sensor 86 is fully embedded in the fifth dielectric layer 52 such that no portion of the sensor 86 is exposed through the second outside surface 52a. This configuration, wherein the sensor 86 is fully embedded in the PCB 84, may be advantageous when the sensor 86 needs to be protected from contamination or the effects of the environment in which it will be used. The configuration embodied in FIG. 6 may also be advantageous when the sensor 86 is configured to function without being in intimate contact with the skin of a patient 82.

Figure 7:
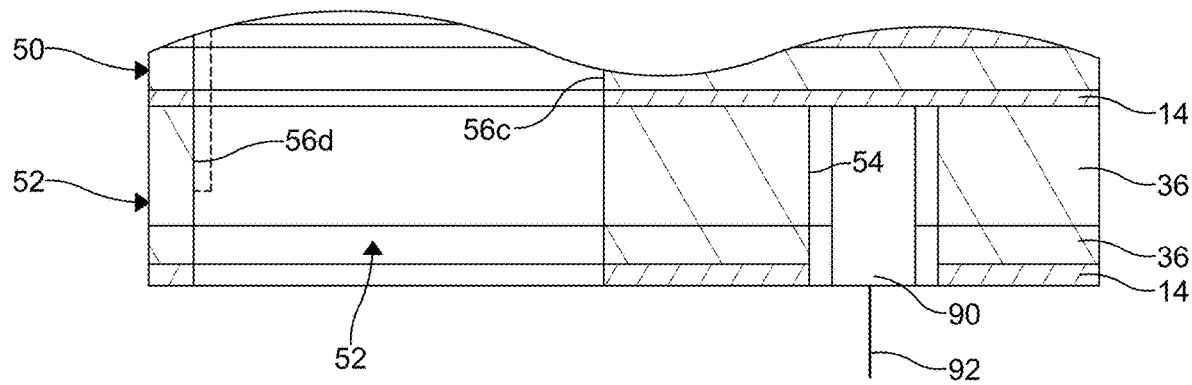
FIG. 7 is an elevational view in cross section of a portion of a fourth embodiment the device illustrated in FIG. 2.

A portion of a fourth embodiment of the improved PCB is shown at 88 in FIG. 7. The PCB 88 is substantially similar to the PCB 30, but includes a sensor 90 inserted in the cavity 54. Like the sensor 32 in the PCB 30, the sensor 90 may be integrally formed with the layers of prepreg 36. The sensor 90 includes a needle 92. The needle 92 may have any desired length and diameter, and is configured for subcutaneous insertion in the patient 82. The needle 92 may be partially coated or encapsulated with a material that allows the needle 92 to function as a subcutaneous sensor to detect and/or measure a physiological parameter, such as cholesterol level, and intra-venous pressure. If desired, the needle 92 may be configured; i.e., be large and robust enough, to penetrate a layer of clothing worn by the patient 82.

Figure 8:
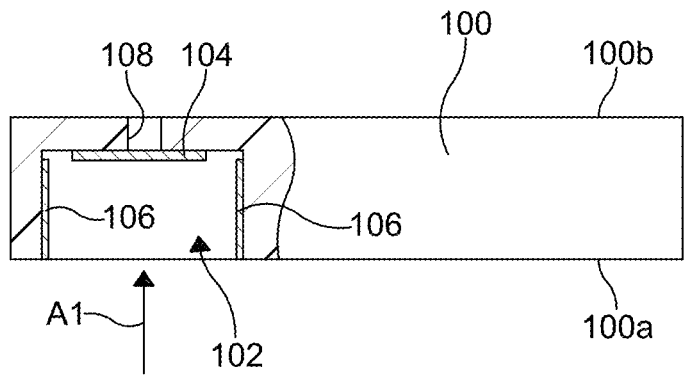
FIG. 8 is an elevational view, partially in cross section, of a first alternate embodiment of a battery well.

Referring now to FIGS. 8 through 11, alternate embodiments of the battery well are shown. FIG. 8 includes a multi-layered PCB 100. The PCB 100 may be substantially similar to the PCB 30. Although not illustrated in FIG. 8, the PCB 100 may include a plurality of dielectric layers, such as the dielectric layers 34, 38, 42, 50, and 52, one or more of the components 43 and 46, and one or more of the sensors 32. A battery well 102 is formed in a surface 100a of a first broad face of the PCB 100 and is configured to receive a battery, such as the battery 58 shown in FIG. 5, inserted in the direction of the arrow A1. The battery 58 may be secured in the battery well 102 by any of the methods described above.

Electrical contact surfaces may be provided at any location in the battery well 102, such as at 104 on a bottom of the battery well 102, and/or at 106 on a side wall of the battery well 102. Additionally, electrical contact surfaces may be integrally formed in the various layers (not shown in FIG. 8) of the PCB 100, as described above in the description of the PCB 30. A hole 108 may be formed from a surface 100b of a second broad face of the PCB 100 and is configured to allow a tool to be inserted therein to push an installed battery out of the PCB 100.

Figure 9:
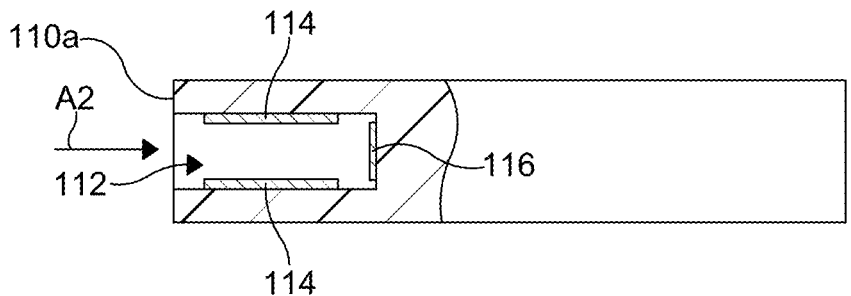
FIG. 9 is an elevational view, partially in cross section, of a second alternate embodiment of a battery well.

FIG. 9 includes a multi-layered PCB 110. The PCB 110 may be substantially similar to the PCB 100. A battery well 112 is formed in a surface 110a of an end face of the PCB 110 and is configured to receive a battery, such as the battery 58 shown in FIG. 5, inserted in the direction of the arrow A2. The battery 58 may be secured in the battery well 112 by any of the methods described above.

Electrical contact surfaces may be provided at any location in the battery well 112, such as at 114 on one or both of a bottom and top of the battery well 112, and/or at 116 on a side wall of the battery well 112. Additionally, electrical contact surfaces may be integrally formed in the various layers (not shown in FIG. 9) of the PCB 110, as described above in the description of the PCB 30.

Figure 10:
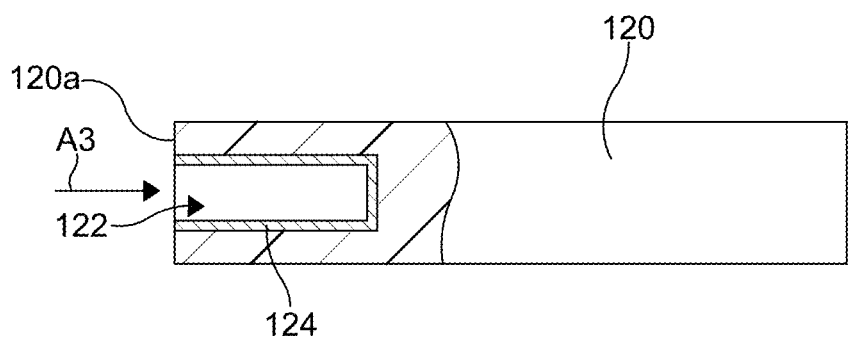
FIG. 10 is an elevational view, partially in cross section, of a third alternate embodiment of a battery well.

FIG. 10 includes a multi-layered PCB 120. The PCB 120 may be substantially similar to the PCB 110, and includes a battery well 122 formed in a surface 120a of an end face of the PCB 120. The battery well 122 is configured to receive a battery housing 124, such as a commercial, off-the-shelf battery housing. The battery housing 124 may be electrically connected to one or more of the electrically conductive layers of the PCB 120. The battery 58 may be inserted in the battery housing 124 in the direction of the arrow A3. The battery 58 may be secured in the battery housing 124 by any of the methods described above.

Figure 11:
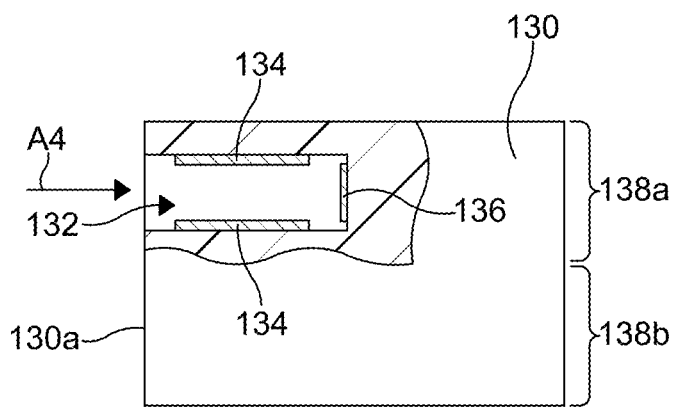
FIG. 11 is an elevational view, partially in cross section, of a fourth alternate embodiment of a battery well.

FIG. 11 includes a multi-layered PCB 130. The PCB 130 is similar to the PCB 100, such that it includes a battery well 132 is formed in a surface 130a of an end face of the PCB 130 and is configured to receive a battery, such as the battery 58 shown in FIG. 5, inserted in the direction of the arrow A4. The battery 58 may be secured in the battery well 132 by any of the methods described above.

Electrical contact surfaces may be provided at any location in the battery well 132, such as at 134 on one or both of a bottom and top of the battery well 132, and/or at 136 on a side wall of the battery well 132. Additionally, electrical contact surfaces may be integrally formed in the various layers (not shown in FIG. 11) of the PCB 130, as described above in the description of the PCB 30.

The PCB 130 differs from the PCBs 100, 110, and 120 in that it is formed having a first portion 138a (the upper portion when viewing FIG. 11), and a second portion 138b (the lower portion when viewing FIG. 11) below the first portion 138a. Although not illustrated in FIG. 11, the PCB 130 may include a plurality of dielectric layers, such as the dielectric layers 34, 38, 42, 50, and 52, in both the first and second portions 138a and 138b.

In this embodiment, the battery well 132 is formed in the first portion 138a. The second portion 138b may include the functional components; i.e., one or more of the components 43 and 46, and one or more of the sensors 32.

One of the advantages of the improved PCBs described herein is that they may be easily configured to be carried, worn, affixed to, inserted into, or implanted in a user or patient 82 such that they are in intimate contact with, or in close proximity to, the skin of the patient 82. For example, the PCB 30' may be affixed to the skin of a patient 82 as shown in FIG. 3. The PCB 30' may be provided with a suitable adhesive (not shown) on a surface thereof, and affixed to the patient 82. Alternatively, the PCB 30' may be affixed to the skin of a patient 82 with adhesive tape (not shown), or an off-the-shelf adhesive bandage (not shown).

As described in detail above, any of the PCBs described herein may include the sensor 90 with the needle 92 that is configured for subcutaneous insertion in the patient 82.

The PCB 30' may also be configured to be attached to or integrally formed with devices that may be worn by the patient 82. Such devices include wrist bands or watches (not shown), bands that may be worn around other parts of the body, including around ankles, legs, arms, the torso, the neck, the head, or any other part of the body, jewelry, eye glasses, and items of clothing.

Any of the improved PCBs described herein, such as the PCB 30', may include the layer of protective material 65, and be configured to be implanted subcutaneously in the patient 82.

The PCB 30' may further be configured to be attached to or integrally formed with items of clothing. For example, the PCB 30' may be attached to the inside surface of a clothing item, placed in a small pocket formed on the inside surface of a clothing item, or sewn into a clothing item. In each example, the PCB 30' is attached to the clothing item such that the PCB 30', and the sensor or sensors 32 therein, are in contact with, or in close proximity to the patient's 82 skin.

The embodiments of the improved PCB described herein all include a power source, such as the battery 58. It will be understood that the improved PCB may be configured without the battery 58 or other internal source of power. Rather, the one or more sensors 32 may be powered wirelessly using any conventional means, such as energy harvesting from motion, heat and/or light, near field inductive power transfer, passive RFID, and high frequency power transfer.

Significantly, the improved PCBs described herein provide advantages to their users, including patients, medical professionals, and other care providers. The PCBs may be formed with all active and passive components, and all sensors within the PCB, thereby allowing the improved PCB to be formed in a smaller overall size relative to a conventional PCB. Electrical performance may be improved due to shorter circuit paths within the improved PCB. Bandwidth within the PCB may be expanded while minimizing noise. The total assembly costs may be reduced. And one PCB configuration may be used with any of a plurality of desired sensors, thereby allowing for faster product development time and reduced manufacturing costs.

The principle and mode of operation of the invention have been described in its preferred embodiments. However, it should be noted that the invention described herein may be practiced otherwise than as specifically illustrated and described without departing from its scope.

What is claimed is:

1. A sensing device comprising:
    a multi-layered printed circuit board (PCB) having at least one conductive layer and at least one dielectric layer, wherein the at least one conductive layer includes a conductive trace and is embedded within the PCB;
    a micro-controller embedded within the PCB attached to the conductive trace;
    a data transmission means embedded within the PCB and connected to the micro-controller; and at least one sensor embedded within at least one of the dielectric layers of the multi-layered PCB and connected to the micro-controller via the embedded conductive trace, the sensor configured to sense at least one physiological parameter in a patient.

2. The sensing device according to claim 1, wherein the PCB is further configured to transmit a signal representative of the physiological parameter sensed by the sensor to a receiver remote from the sensing device.

3. The sensing device according to claim 2, wherein the receiver is a portable electronic device.

4. The sensing device according to claim 3, wherein the portable electronic device is one of smart phone and a computer.

5. The sensing device according to claim 1, wherein the sensor is configured to sense one of temperature, heart rate, blood pressure, oxygen saturation of blood, respiration, electrical activity of a heart, body movement, blood attributes, internal body pressures, internal organ activity, glucose levels, perspiration, neural activity, neural stimulation, and infection.

6. The sensing device according to claim 1, further comprising a cavity formed in at least one of the dielectric layers of the multi-layered PCB, wherein the sensor is inserted into the formed cavity.

7. The sensing device according to claim 1, wherein the sensor is partially embedded within at least one of the dielectric layers of the multi-layered PCB such that a first portion of the sensor is one of integrally formed within at least one of the dielectric layers of the multi-layered PCB and inserted into a cavity formed in at least one of the dielectric layers of the PCB, and wherein a second portion of the sensor one of (i) extends outwardly of an outer surface of the PCB and (ii) does not extend outwardly of the outer surface of the PCB but is exposed through the outer surface of the PCB.

8. The sensing device according to claim 1, wherein the sensor includes a needle extending outwardly of an outside surface of the PCB, the needle configured for subcutaneous insertion in the patient.

9. The sensing device according to claim 8, wherein the needle is partially coated with a material that allows the needle to function as a subcutaneous sensor to one or both of detect and measure a physiological parameter in the patient.

10. The sensing device according to claim 1, wherein the sensor is configured to be powered wirelessly by a source of electrical energy located outside of the sensing device.

11. The sensing device according to claim 1, wherein the data transmission means is configured to transmit a signal representative of the physiological parameter sensed by the sensor to a receiver remote from the sensing device.

12. The sensing device according to claim 1, further comprising a cavity formed through a portion of at least one dielectric layer configured to receive an associated battery, wherein the cavity includes at least one electrical contact surface integrally formed within at least one layer of the multi-layer PCB.

13. A printed circuit board (PCB) comprising:
a substrate comprising at least one dielectric layer, at least one conductive layer, an internal conductive trace and a power conditioning circuit formed therein;
a micro-controller embedded within the substrate and attached to the internal conductive trace;
a sensor embedded within at least one dielectric layer of the substrate and connected to the micro-controller via the internal conductive trace, the sensor configured to sense one or more physiological parameters in a patient; and
a data transmission means embedded within the substrate and connected to the micro-controller, the data transmission means configured to transmit a signal representative of the physiological parameter sensed by the sensor to a receiver remote from the sensing device.

14. The printed circuit board according to claim 13, wherein the sensor includes a needle extending outwardly of an outside surface of the PCB, the needle configured for subcutaneous insertion in the patient.

15. The printed circuit board according to claim 14, wherein the needle is partially coated with a material that allows the needle to function as a subcutaneous sensor to one or both of detect and measure a physiological parameter in the patient.

16. The printed circuit board according to claim 13, wherein the receiver is a portable electronic device.

17. The printed circuit board according to claim 13, wherein the sensor is configured to sense one of temperature, heart rate, blood pressure, oxygen saturation of blood, respiration, electrical activity of a heart, body movement, blood attributes, internal body pressures, internal organ activity, glucose levels, perspiration, neural activity, neural stimulation, and infection.

18. The printed circuit board according to claim 13, wherein the sensor is one of integrally formed within at least one dielectric layer of the substrate and inserted into a cavity formed in at least one dielectric layer of the substrate.

19. The printed circuit board according to claim 13, wherein the sensor is partially embedded within at least one dielectric layer of the substrate such that a portion of the sensor is one of integrally formed within at least one dielectric layer of the substrate and inserted into a cavity formed in at least one dielectric layer of the substrate, and wherein a portion of the sensor one of extends outwardly of an outer surface of the substrate, and does not extend outwardly of the outer surface of the PCB but is exposed through the outer surface of at least one dielectric layer of the substrate.

20. The printed circuit board according to claim 13, wherein the sensor is configured to be powered wirelessly by a source of electrical energy located outside of the sensing device.

21. A sensing device comprising:
a multi-layered printed circuit board (PCB) having at least one conductive layer and at least one dielectric layer, wherein the at least one conductive layer and the at least one dielectric layer are integrally formed within the PCB, and wherein the at least one conductive layer includes a conductive trace;
a micro-controller attached to the conductive trace of the at least one conductive layer;
a data transmission means connected to the micro-controller; and
at least one sensor integrally formed within at least one of the dielectric layers of the multi-layered PCB and connected to the micro-controller via the conductive trace of the at least one conductive layer, the sensor configured to sense at least one physiological parameter in a patient.

22. The sensing device according to claim 21, wherein the conductive trace, the micro-controller, the data transmission means, and the at least one sensor are internal to the PCB.

23. The sensing device according to claim 21, wherein the micro-controller and the data transmission means are mounted to an internal layer of the PCB.

\* \* \* \* \*